(12) United States Patent
Brajnovic

(10) Patent No.: US 8,157,563 B2
(45) Date of Patent: *Apr. 17, 2012

(54) GUIDE DEVICE ABLE TO INTERACT WITH A NUMBER OF SLEEVES DISPOSED IN A TOOTH TEMPLATE

(75) Inventor: Izidor Brajnovic, Rydal (SE)

(73) Assignee: Nobel Biocare Services AG, Glattbrugg (CH)

( * ) Notice: Subject to any disclaimer, the term of this patent is extended or adjusted under 35 U.S.C. 154(b) by 0 days.

This patent is subject to a terminal disclaimer.

(21) Appl. No.: 12/538,811

(22) Filed: Aug. 10, 2009

(65) Prior Publication Data

US 2009/0298009 A1 Dec. 3, 2009

Related U.S. Application Data

(63) Continuation of application No. 11/573,193, filed as application No. PCT/SE2005/001074 on Jul. 4, 2005, now Pat. No. 7,572,125.

(30) Foreign Application Priority Data

Aug. 5, 2004 (SE) ...................................... 0401984

(51) Int. Cl.
*A61C 1/08* (2006.01)
(52) U.S. Cl. ........................................................ 433/75
(58) Field of Classification Search ............... 433/72, 433/74, 75, 76; 606/96
See application file for complete search history.

(56) References Cited

U.S. PATENT DOCUMENTS

| 4,364,381 A * | 12/1982 | Sher et al. ........................ 606/96 |
| 5,302,122 A | 4/1994 | Milne |
| 5,320,529 A | 6/1994 | Pompa |
| 5,362,236 A | 11/1994 | Branemark |
| 5,564,926 A | 10/1996 | Branemark |
| 5,743,916 A | 4/1998 | Greenberg et al. |

(Continued)

FOREIGN PATENT DOCUMENTS

EP 1317910 A1 6/2003

(Continued)

OTHER PUBLICATIONS

International Search Report for Application No. PCT/SE 2005/001074.

*Primary Examiner* — Ralph Lewis
(74) *Attorney, Agent, or Firm* — Knobbe, Martens, Olson & Bear, LLP.

(57) ABSTRACT

A guide device is provided that can interact with a number of sleeves of a tooth template. The guide device can include a handle part, a support part, and a guide part. The handle part can include first and second parts. The first part can be connectable to the second part, and the second part can include a space having a variable size. The variable size of the space can be determined by the position of the first part relative to the second part. The supporting part can be sized and configured to engage the space of the handle for allowing selective positioning of the supporting part relative to the handle part. The guide part can be connectable to the supporting part with the guide part being operative to align a tool for use in the dental treatment.

25 Claims, 2 Drawing Sheets

U.S. PATENT DOCUMENTS

| | | |
|---|---|---|
| 5,967,777 A | 10/1999 | Klein et al. |
| 5,989,025 A | 11/1999 | Conley |
| 6,099,311 A | 8/2000 | Wagner et al. |
| 6,099,331 A | 8/2000 | Kikkawa et al. |
| 6,287,119 B1 | 9/2001 | van Nifterick et al. |
| 7,572,125 B2 * | 8/2009 | Brajnovic .................. 433/75 |
| 2004/0142300 A1 | 7/2004 | Aravena |
| 2005/0170311 A1 | 8/2005 | Tardieu et al. |
| 2010/0009314 A1 | 1/2010 | Tardieu et al. |

FOREIGN PATENT DOCUMENTS

| | | |
|---|---|---|
| FR | 2836372 A1 | 8/2003 |
| WO | WO 01/58379 A1 | 8/2001 |

* cited by examiner

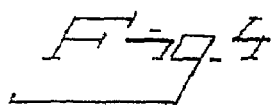
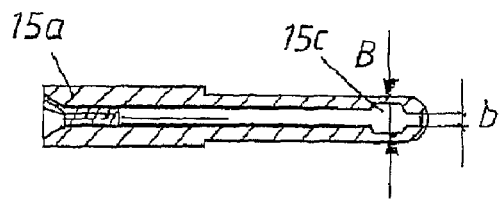
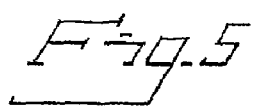
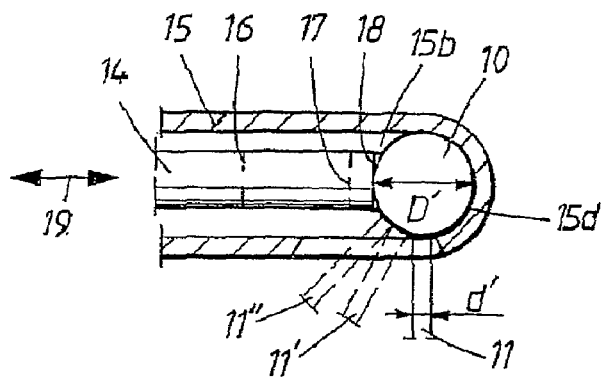
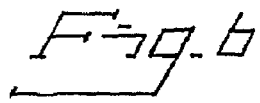
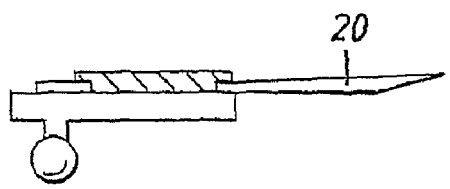
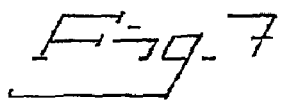
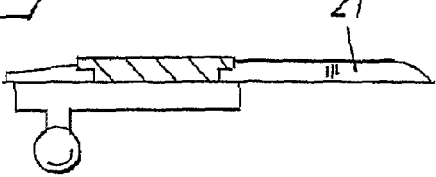

GUIDE DEVICE ABLE TO INTERACT WITH A NUMBER OF SLEEVES DISPOSED IN A TOOTH TEMPLATE

CROSS-REFERENCE TO RELATED APPLICATIONS

This application is a continuation of U.S. National Phase Application No. 11/573,193, filed on Jun. 6, 2007, now U.S. Pat. No. 7,572,125 which is a U.S. National Phase of International Application No. PCT/SE2005/001074, filed Jul. 4, 2005, which claims priority to Swedish Patent Application No. 0401984-0, filed Aug. 5, 2004, each of which is hereby incorporated by reference in its entirety.

BACKGROUND

1. Field of the Invention

The present invention relates generally to dental treatments, and more specifically, to a guide device that can interact with a number of sleeves disposed in a tooth template or surgical template and includes a guide part which can be fitted to a corresponding sleeve which is connected to or forms part of a handle part for fitting to the corresponding sleeve of the guide part.

2. Description of the Related Art

In the dental field, it is known that there are varying degrees of difficulty for dental treatments, and that the difficulty of such treatments depends on the various positions of the teeth and of the treatment sites in the oral cavity. The teeth and the spaces in the front parts of the oral cavity are easily accessible, whereas problems can arise in achieving rapid and effective treatment in the case of teeth and spaces in the inner parts of the oral cavity.

If a shaft-mounted guide part or shaft-mounted guide parts are desired for the inner teeth and spaces, problems can arise both in fitting the guide part or guide parts and in preventing the shaft protruding from the guide part from hindering the actual work and causing significant discomfort to the patient.

SUMMARY

In accordance with an aspect of some embodiments, it is desirable that the equipment used to perform dental treatments should be simple and easy to operate. Further, it may also be desirable that such equipment be operated with only small actuation movements. Furthermore, such equipment should facilitate change between different guide parts and shafts during the course of the work. Finally, there is also a need for the equipment used to be easy to clean and sterilize.

In some embodiments, there is provided a guide that can, inter alia, be used in connection with rapid dental treatments, such as dental treatments in accordance with the "Teeth in an Hour" concept. When implants are fitted in these types of rapid treatments, surgical templates with sleeves are often used. These surgical templates can include guides for guide parts which in turn guide the instrument in question, such as a drill, knife, etc., in connection with the insertion of the implant. The position of each of the sleeves in the surgical template is planned using a computer, in a manner known in the art.

The guide part can be such that its external diameter corresponds to an internal diameter of the corresponding tooth template sleeve. The guide part can be made up of a guide sleeve. The guide sleeve can have a central aperture that can include a guide for a desired instrument, such as a drill. The guide part can be supported on a shaft so that it can easily be moved between the various positions for the tooth template sleeves.

In accordance with another aspect of embodiments, the guide part can be disposed with a ball bearing race and the handle part can include or interact with an actuation part that can be able to interact with the ball bearing race. In this regard, different relative positions between the handle part and the guide part can be lockably set up.

In a preferred embodiment, the handle part can comprise first and second parts which can be displaceable in relation to each other. The first part can include an internal thread and the second part can include an external thread which can interact with the internal thread. The second part can include a part which receives the ball bearing race.

On activation, the first part can be configured to take up different longitudinal displacement positions in relation to the ball bearing race when the latter is inserted or located in a space assigned to the ball bearing race in the second part. In a first longitudinal displacement position for the first part, the latter can be configured so as to allow the insertion of the ball bearing race in the space. In a second longitudinal displacement position for the first part, the latter can be arranged so as to prevent the removal of the ball bearing race from the space, but to allow rotary movements of the ball bearing race relative to the second part. In a third longitudinal displacement position, the first part can lock the ball bearing race to the second part and prevent rotation of the ball bearing race relative to the second part.

In some embodiments, it is preferably that a diameter or cross-sectional area of the guide part, which supports a spherical part in the ball bearing race on a supporting part, be significantly smaller than the diameter or cross-sectional area of the spherical part. The extent to which the diameter of the guide part is smaller than the diameter of the spherical part can lie within the range 50-75%.

The second part can include a lateral recess in the space assigned to the ball bearing race. The lateral recess can be sized and configured with a first width and a second width. The first width can exceed the diameter or cross-sectional area of the spherical part. Further, the second width can be less than the diameter or cross-sectional area of the spherical part, but exceed the diameter or cross-sectional area of the supporting part. In this way, the first and second parts of the handle can be rotatable relative to the guide part for providing different height and rotation positions. It is contemplated that the guide part and the handle part can be lockable relative to each other in the height and rotation positions.

What is proposed herein makes an advantageous adjustment function for the handle part possible. Thus, the guide part can be fitted in a corresponding guide or tooth sleeve, and interference between the handle part and the dental work can be prevented while minimizing discomfort to the patient. Further, small actuation movements can be made in order to attain the different position settings. Finally, the various parts can easily be disassembled for cleaning and sterilization.

BRIEF DESCRIPTION OF THE DRAWINGS

The abovementioned and other features of the inventions disclosed herein are described below with reference to the drawings of the preferred embodiments. The illustrated embodiments are intended to illustrate, but not to limit the inventions. The drawings contain the following figures:

FIG. 4 is a cross-sectional longitudinal view of the first and second parts of the handle part in an assembled configuration.

FIG. 5 is a cross-sectional longitudinal view of the second part shown in FIG. 2, wherein a sphere in place and different longitudinal displacement positions are shown in principle for the first part relative to the second part and a ball bearing race.

FIGS. 6 and 7 are lateral views instruments (shown as knives) which can be fitted to the guide part.

DETAILED DESCRIPTION

Figure 1:
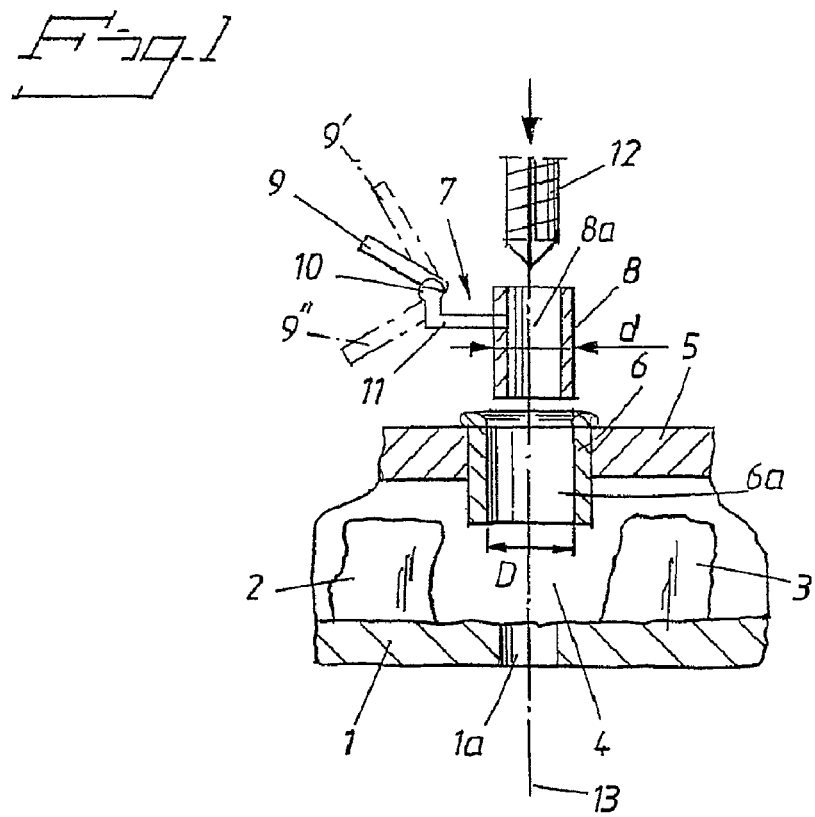
FIG. 1 is a vertical cross-sectional view of parts of a mandible with teeth and a tooth template arranged in relation to the teeth with a guide sleeve and a guide device with a guide sleeve and handle part of a drill, in accordance with an embodiment.

FIG. 1 is a vertical cross-sectional view of a mandible 1. The mandible 1 supports teeth 2 and 3 and also exhibits a space 4 situated between said teeth. A template 5, such as a tooth template, surgical template, etc., can be fitted to the teeth in a manner known in the art. The template 5 can include one or more guide sleeves 6. The guide sleeve 6 can have a central aperture 6a with a diameter D. The positions of the guide sleeves 6 can be pre-calculated by means of a computer (not shown) in a manner known in the art.

The embodiment shown in FIG. 1 can include a guide device 7 having a guide part 8 and a handle part 9. The guide and handle parts 8, 9 can be connected to each other via a ball bearing race 10 and a part 11 supporting the handle part 9. The guide part 8 can include a sleeve having an external diameter d which is only slightly smaller than the internal diameter D of the guide sleeve 6. The guide part 8 can thus be fitted into the aperture 6a of the guide sleeve 6. The guide part 8 can in turn be provided with a central aperture 8a, into which a drill 12 can be fitted when the guide part 8 is lowered into the guide sleeve 6 for uptake by a drill hole 1a in the mandible. Further, the sleeve of the guide part 8 can also interact with the guide sleeve 6 such that when the template 5 and guide sleeve 6 are fitted, the handle part 9 can be adjustable depending on the given sleeve 6 of the tooth template 5 where dental work is being performed in the oral cavity. For example, the handle part 9 can protrude essentially straight out of the oral cavity during work on front teeth and diagonally outwards and upwards/downwards during work on inner teeth.

The drill hole can constitute a hole uptake for an implant in a manner known in the art. Thanks to the ball bearing race 10, the handle part 9 can be rotated to different height positions. Exemplary height positions are illustrated in FIG. 1 as 9' and 9". In addition, the guide part 8 can be rotatable relative to the guide sleeve 6 around a longitudinal axis 13 which can be common to the guide part 8, the guide sleeve 6, the drill 12, and the drill hole 1a.

Figure 2:
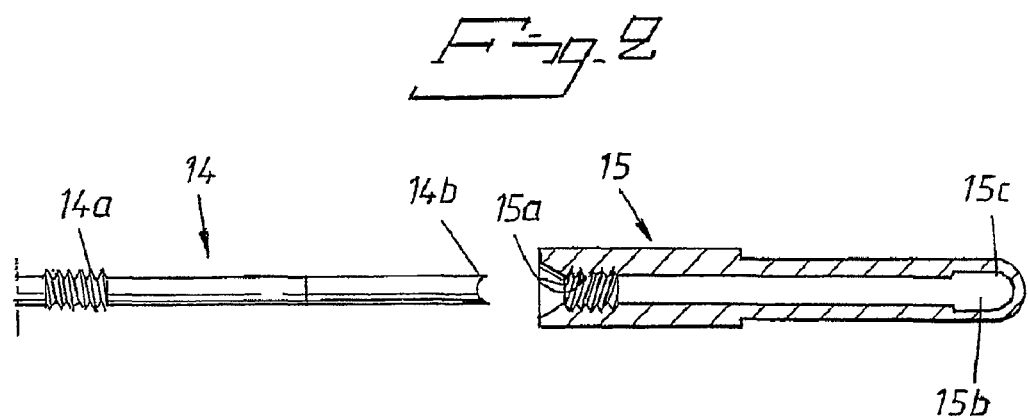
FIG. 2 is an exploded cross-sectional side view of the first and second parts in the handle part, according to an embodiment.

In accordance with the embodiment shown in FIG. 2, the handle part 9 can include a first part 14 and a second part 15. The first part 14 can be provided at its back end with an external thread 14a and can be provided in its front part with an interaction part 14b. The interaction part 14b can allow the first part 14 to interact with the ball bearing race 10 referred to above. In its back parts the second part 15 can exhibit an internal thread 15a, in which the first part 14 can be screwed into the second part 15 by means of its thread 14a. At its front end, the second part 15 can include an internal space 15b. In addition, the second part 15 can include a lateral recess 15c, through which the ball bearing race 10 (see FIG. 1) can be inserted into the space 15b with the supporting part 11 extending outside to the guide sleeve 6.

Figure 3:
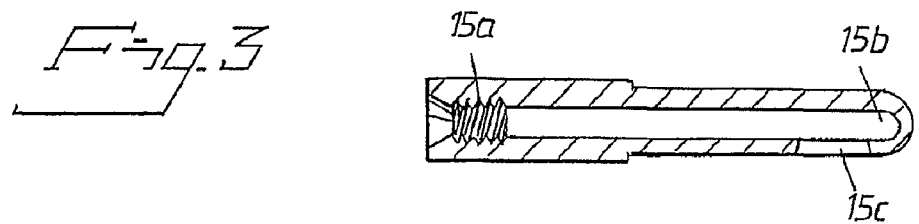
FIG. 3 is a cross-sectional longitudinal view of the second part illustrated in FIG. 2, which is rotated by 90° relative to the view in FIG. 2.

FIG. 3 shows said lateral recess 15c and the space 15b of the second part 15 in a view that is rotated by 90° relative to FIG. 2.

In accordance with another embodiment, FIG. 4 shows the design of the lateral recess 15c. The lateral recess 15c can define a first width B and a second width b. The first width B can be sized to exceed the diameter or width of a sphere in the ball bearing race 10, while the smaller width b can be less than the diameter of the sphere, but exceed the diameter or cross-sectional area of the supporting part. The sphere can thus be inserted into the space 15b at the second width B and advanced towards the front end of the second part into the space 15b (see FIG. 2).

In accordance with the embodiment illustrated in FIG. 5, the first part 14 can be assigned different longitudinal displacement positions relative to the second part 15. A first longitudinal displacement position 16 can allow the sphere of the ball bearing race 10 to be inserted into the space 15b and pushed forward or advanced into the space 15b. In a second longitudinal displacement position 17, the first part 14 can makes it impossible for the sphere 10 to be removed from the space 15b. The sphere can be rotatable in the space, however, in the second longitudinal displacement position 17 of the first part 14.

In a third position 18, the sphere of the ball bearing race 10 can be locked to a front internal wall 15d of the second part 15. In positions 17 and 18, the supporting member 11 can extend to the outside via the lateral recess 15c. The second width b can exceed the diameter d' or cross-sectional area of the supporting member 11, thereby allowing the supporting member 11 to extend outwardly from the lateral recess 15c. The rotatability of the sphere in the second position 17 allows the supporting member in FIG. 5 to extend to an optionally adjusted position in the plane of the paper. Two further rotational positions have been shown in FIG. 5 as 11' and 11".

Depending on the choice of the width b and the diameter d', the supporting member 11 can also be actuated relative to the handle part 9, or vice versa, even at right angles to the plane of the figure in accordance with FIG. 5. The sphere of the ball bearing race 10 can have a diameter D'. The diameter D' of the sphere can be less than the first width B, but exceed the second width b. It can be seen that the construction described above makes possible a large number of individual rotational positions between the second part 15 and the guide part 8. The actuation directions for the first part 14 relative to the second part 15 are shown as 19 in FIG. 5.

FIGS. 6 and 7 are intended to show in principle that the guide part 8 can be a guiding member for instruments other than drills, such as knives, for example. In FIGS. 6 and 7, the blades of the knives have been indicated as 20 and 21.

Although these inventions have been disclosed in the context of certain preferred embodiments and examples, it will be understood by those skilled in the art that the present inventions extend beyond the specifically disclosed embodiments to other alternative embodiments and/or uses of the inventions and obvious modifications and equivalents thereof. In addition, while several variations of the inventions have been shown and described in detail, other modifications, which are within the scope of these inventions, will be readily apparent to those of skill in the art based upon this disclosure. It is also contemplated that various combination or sub-combinations of the specific features and aspects of the embodiments may be made and still fall within the scope of the inventions. It should be understood that various features and aspects of the disclosed embodiments can be combined with or substituted for one another in order to form varying modes of the disclosed inventions. Thus, it is intended that the scope of at least some of the present inventions herein disclosed should not be limited by the particular disclosed embodiments described above.

What is claimed is:

1. A guide device for use in dental treatment to facilitate alignment of a tool with at least one template guide sleeve of a template, the device comprising:
- a handle part including first and second parts, the first part being connectable to the second part, the second part including a space having a variable size, the variable size of the space being determined by the position of the first part relative to the second part;
- a supporting part comprising first and second ends, the first end thereof being positionable in the space of the handle part; and
- a part guide sleeve defining an outer surface and a central aperture, the outer surface of the part guide sleeve being coupled to the second end of the supporting part, the part guide sleeve being positionable within the template guide sleeve, the central aperture of the part guide sleeve being configured to receive the tool;
- wherein the first end of the supporting part can be fixed within the space of the handle part upon movement of the distal end of the first part of the handle part into the space for locking the orientation of the supporting part relative to the handle part, and wherein the first part of the handle part includes an internal thread and the second part of the handle part includes an external thread which can interact with the internal thread to adjust the variable size of the space.

2. The guide device of claim 1, wherein the first and second parts of the handle part are separable from each other to facilitate cleaning and sterilization.

3. The guide device of claim 1, wherein slight relative movement between the first and second parts is operative to allow one of replacement of the part guide sleeve and reorientation of the handle part relative to the part guide sleeve.

4. The guide device of claim 1, wherein the first part of the handle part is sized and configured to be oriented at different longitudinal displacement positions relative to the second part to vary the size of the space, the first part having a longitudinal displacement position wherein the supporting part can be at least partially engaged in the space, the first part having another longitudinal displacement position wherein the first part generally fixes the orientation of the supporting part relative to the handle part.

5. The guide device of claim 1, wherein the first end of the supporting part includes a spherical part being insertable into the space of the second part of the handle part, the variable size of the space being adjustable to fix an orientation of the spherical part within the space.

6. The guide device of claim 5, wherein the second part further includes a lateral recess disposed adjacent to the space, the lateral recess being sized and configured with a first width being approximately greater than a diameter of the spherical part, the lateral recess further being sized and configured with a second width being less than the diameter of the spherical part and greater than a diameter of the supporting part.

7. The guide device of claim 1, wherein the part guide sleeve is monolithically formed with the supporting part.

8. The guide device of claim 1, wherein the central aperture of the part guide sleeve defines a longitudinal axis that is aligned with a longitudinal axis of the template guide sleeve when the part guide sleeve is positioned therein.

9. The guide device of claim 8, wherein the central aperture of the part guide sleeve is configured to receive the tool for aligning a longitudinal axis of the tool with longitudinal axes of the part guide sleeve and the template guide sleeve.

10. The guide device of claim 9, wherein the longitudinal axis of the central aperture of the part guide sleeve is common to the template guide sleeve when the part guide sleeve is inserted into the template guide sleeve.

11. A guide device for use in dental treatment to facilitate alignment of a tool with at least one template guide sleeve of a template, the device comprising:
- a handle part including first and second parts, the first part being defining proximal and distal ends, the second part defining a central aperture and a space located at the distal end thereof, the first part being insertable within the aperture of the second part and threadably connectable to the second part, the distal end of the first part being selectively moveable into or out of the space of the second part to vary a size of the space of the second part; and
- a supporting part comprising first and second ends, the first end thereof being positionable in the space of the handle part, the second end being coupled with a part guide sleeve, the part guide sleeve extending from the second end of the supporting part and defining a central aperture, the part guide sleeve being positionable within the template guide sleeve, the central aperture of the part guide sleeve being configured to receive the tool;
- wherein the first end of the supporting part can be fixed within the space of the handle part upon movement of the distal end of the first part of the handle part into the space for locking the orientation of the supporting part relative to the handle part.

12. The guide device of claim 11, wherein the proximal end of the first part of the handle part is rotatable to cause the first part to move axially relative to the second part such that the distal end of the first part moves relative to the space of the second part.

13. The guide device of claim 12, wherein the first part of the handle part includes an internal thread and the second part of the handle part includes an external thread which can interact with the internal thread to adjust the variable size of the space.

14. The guide device of claim 12, wherein the first part of the handle part includes an external thread and the second part of the handle part includes an internal thread which can interact with the external thread to adjust the variable size of the space.

15. The guide device of claim 11, wherein the part guide sleeve is monolithically formed with the supporting part.

16. The guide device of claim 11, wherein the first end of the supporting part includes a spherical part being insertable into the space of the second part of the handle part.

17. The guide device of claim 11, wherein the central aperture of the part guide sleeve defines a longitudinal axis that is aligned with a longitudinal axis of the template guide sleeve when the part guide sleeve is positioned therein.

18. A guide assembly for facilitating the use of a tool in a dental treatment, the assembly comprising:
- a template comprising at least one template guide sleeve, the template guide sleeve defining a longitudinal axis; and
- a guide device for aligning the tool with the template guide sleeve, the guide device comprising:

a part guide sleeve defining a central aperture and an outer surface, the part guide sleeve being configured to be positioned within the template guide sleeve, the central aperture of the part guide sleeve being configured to receive the tool;

a supporting part comprising first and second ends, the second end thereof being coupled to the outer surface of the part guide sleeve; and a handle part comprising first and second parts, the first part being connectable to the second part, the second part including a space having a variable size for receiving at least a portion of the first end of the supporting part, the variable size of the space being determined by the position of the first part relative to the second part, wherein the first part of the handle part includes an internal thread and the second part of the handle part includes an external thread which can interact with the internal thread to adjust the variable size of the space.

19. The guide assembly of claim 18, wherein the part guide sleeve is monolithically formed with the supporting part.

20. The guide assembly of claim 18, the first end of the supporting part comprises a generally spherical head.

21. The guide assembly of claim 20, wherein the space of the second part of the handle part is configured to receive the spherical head of the first end of the supporting part, the first part of the handle part being movable between at least first and second positions, wherein at the first position the handle part is movable relative to the spherical head of the supporting part and at the second position the first part of the handle part contacts the spherical head to lock the orientation of the supporting part relative to the handle part.

22. The guide assembly of claim 18, wherein the central aperture defines a longitudinal axis that can be aligned with the longitudinal axis of the template guide sleeve when the part guide sleeve is positioned in the template guide sleeve.

23. The guide assembly of claim 22, wherein the central aperture of the part guide sleeve is configured to align a longitudinal axis of the tool with the longitudinal axes of the part guide sleeve and the template guide sleeve.

24. A guide device for use in dental treatment to facilitate alignment of a tool with at least one template guide sleeve of a template, the device comprising:

a handle part including first and second parts, the first part being connectable to the second part, the second part including a space having a variable size, the variable size of the space being determined by the position of the first part relative to the second part;

a supporting part comprising first and second ends, the first end thereof being positionable in the space of the handle part; and a part guide sleeve defining an outer surface and a central aperture, the outer surface of the part guide sleeve being coupled to the second end of the supporting part, the part guide sleeve being positionable within the template guide sleeve, the central aperture of the part guide sleeve being configured to receive the tool;

wherein the first end of the supporting part can be fixed within the space of the handle part upon movement of the distal end of the first part of the handle part into the space for locking the orientation of the supporting part relative to the handle part, and wherein the first part of the handle part includes an external thread and the second part of the handle part includes an internal thread which can interact with the external thread to adjust the variable size of the space.

25. A guide assembly for facilitating the use of a tool in a dental treatment, the assembly comprising:

a template comprising at least one template guide sleeve, the template guide sleeve defining a longitudinal axis; and a guide device for aligning the tool with the template guide sleeve, the guide device comprising:

a part guide sleeve defining a central aperture and an outer surface, the part guide sleeve being configured to be positioned within the template guide sleeve, the central aperture of the part guide sleeve being configured to receive the tool;

a supporting part comprising first and second ends, the second end thereof being coupled to the outer surface of the part guide sleeve; and a handle part comprising first and second parts, the first part being connectable to the second part, the second part including a space having a variable size for receiving at least a portion of the first end of the supporting part, the variable size of the space being determined by the position of the first part relative to the second part, wherein the first part of the handle part includes an external thread and the second part of the handle part includes an internal thread which can interact with the external thread to adjust the variable size of the space.

* * * * *